(12) United States Patent
Karram et al.

(10) Patent No.: US 6,238,383 B1
(45) Date of Patent: May 29, 2001

(54) APPARATUS AND METHOD TO FACILITATE INTERMITTENT SELF-CATHETERIZATION BY A USER

(75) Inventors: Mickey M. Karram, Cincinnati, OH (US); Bryan D. Knodel, Flagstaff, AZ (US)

(73) Assignee: Medical Device Solutions, Mesa, AZ (US)

( * ) Notice: Subject to any disclaimer, the term of this patent is extended or adjusted under 35 U.S.C. 154(b) by 0 days.

(21) Appl. No.: 09/549,680

(22) Filed: Apr. 14, 2000

Related U.S. Application Data
(60) Provisional application No. 60/144,858, filed on Jul. 20, 1999.

(51) Int. Cl.[7] .................................................. A61M 27/00
(52) U.S. Cl. ............................................. 604/544; 600/29
(58) Field of Search .................. 600/29, 585; 604/544, 604/164.13; 128/885, DIG. 25

(56) References Cited

U.S. PATENT DOCUMENTS

| | | | |
|---|---|---|---|
| 3,467,088 | 9/1969 | Robinson | 128/130 |
| 3,490,456 | 1/1970 | Kortum | 128/348 |
| 3,590,816 | 7/1971 | Rosenthal | 128/130 |
| 3,908,663 | 9/1975 | Viek | 128/349 |
| 4,155,364 | 5/1979 | Boxer | 128/349 |
| 4,738,667 | 4/1988 | Galloway | 604/281 |
| 5,025,799 | 6/1991 | Wilson | 128/772 |
| 5,111,829 | 5/1992 | Alvarez de Toledo | 128/772 |
| 5,238,004 | 8/1993 | Sahatjian et al. | 128/772 |
| 5,282,784 | 2/1994 | Willard | 604/8 |
| 5,290,229 | 3/1994 | Paskar | 604/95 |
| 5,322,501 | 6/1994 | Mahmud-Durrani | 604/8 |
| 5,354,263 | 10/1994 | Coll | 604/8 |
| 5,562,622 | 10/1996 | Tihon | 604/105 |
| 5,681,274 | 10/1997 | Perkins et al. | 604/8 |
| 5,738,654 | 4/1998 | Tihon | 604/105 |
| 5,865,815 | 2/1999 | Tihon | 604/280 |

FOREIGN PATENT DOCUMENTS
SU 095593A 11/1982 (RU).

OTHER PUBLICATIONS
Harold Ellis, THE LANCET, *Self-Retaining Polyethylene Catherter for Females*, 981 (May 6, 1961)

Primary Examiner—Samuel G. Gilbert
Assistant Examiner—Joseph A Cadugan
(74) Attorney, Agent, or Firm—Chittaranjan N. Nirmel; Jones Jain, LLP

(57) ABSTRACT

A guidewire or other guide element has an elastically deformable distal end portion that is formed to have an unstrained shape or other features selected to allow the guide element to be safely retained inside a female's urinary bladder after placement therein via a tubular catheter by a doctor. The proximal end of the guide element extends out of her urethra to be easily accessible to her. When she needs to urinate, she passes the proximal end of the guide element into the distal end of another tubular catheter by herself and guides the catheter along the guide element into her bladder to pass out urine through the catheter. When her condition has improved, she or her doctor can withdraw the guide element via a similar catheter.

26 Claims, 6 Drawing Sheets

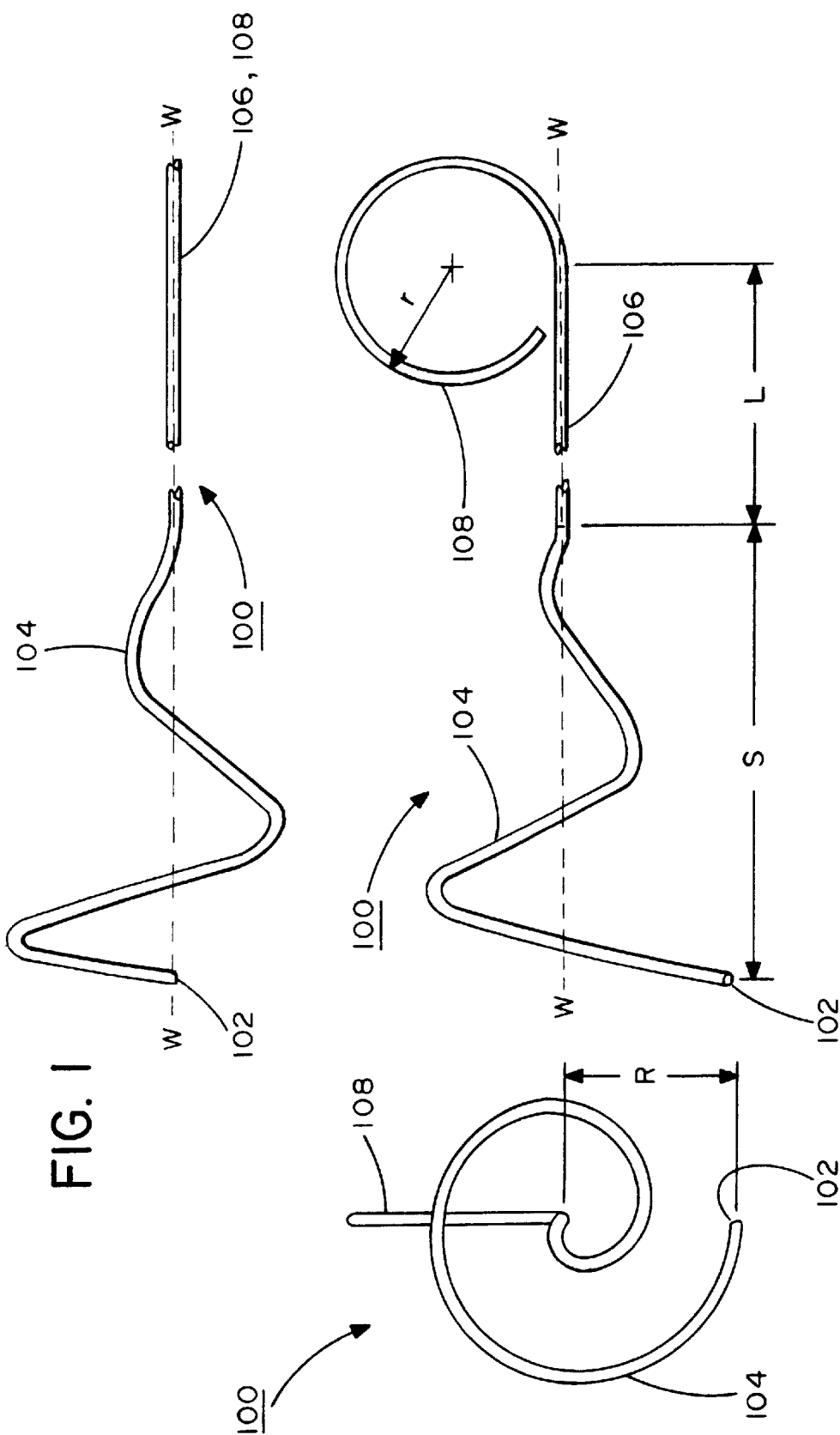

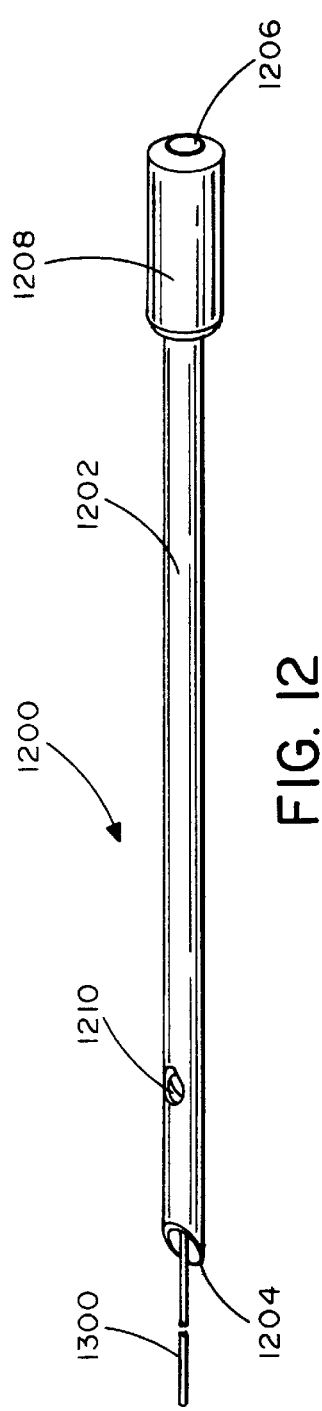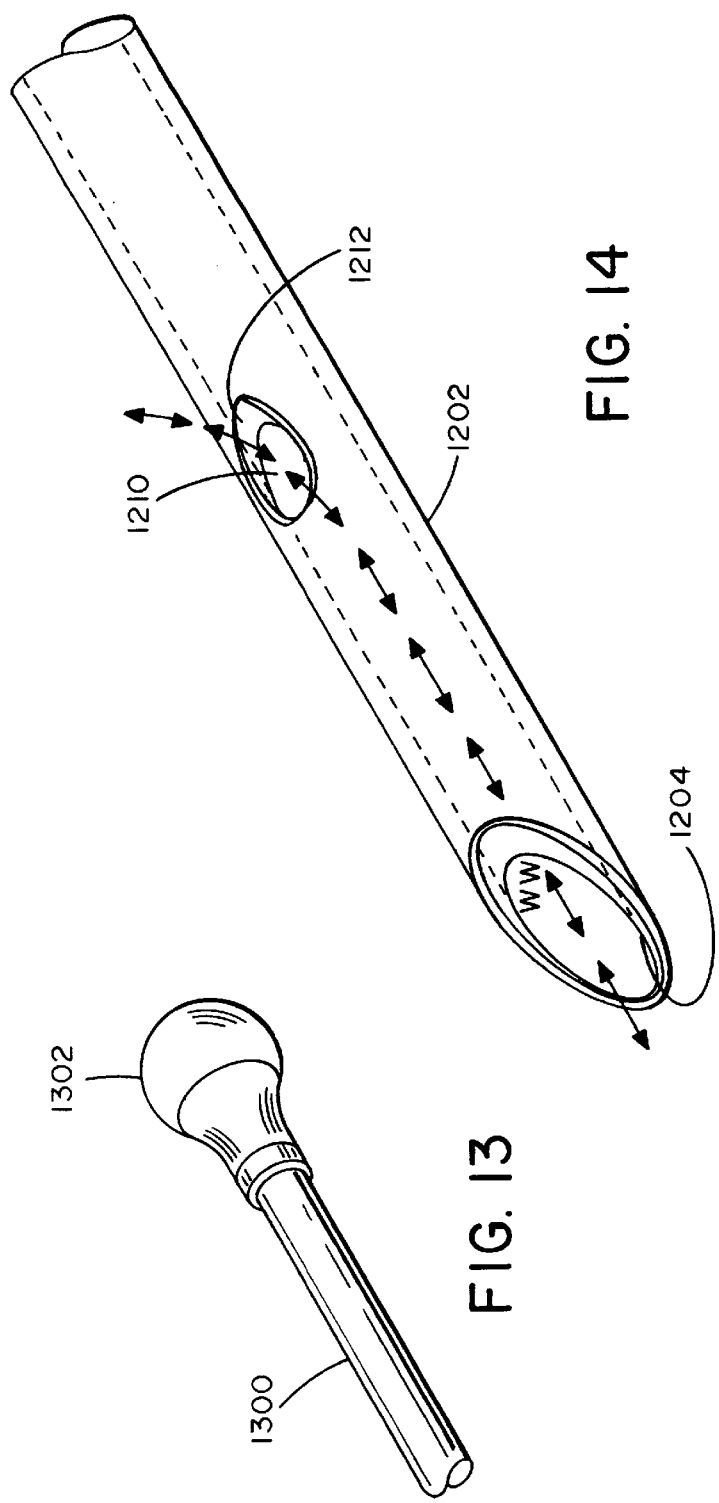

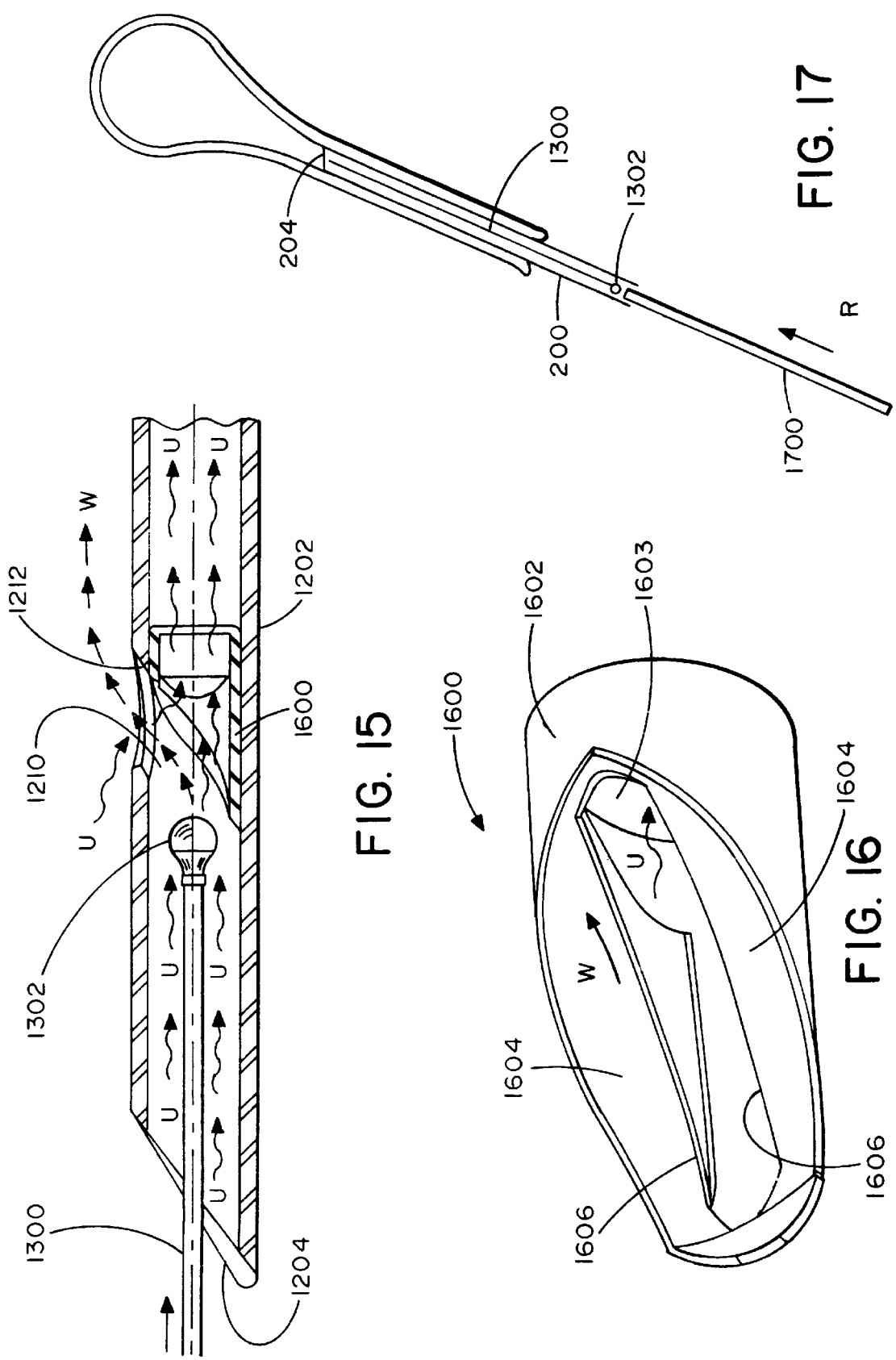

APPARATUS AND METHOD TO FACILITATE INTERMITTENT SELF-CATHETERIZATION BY A USER

This application claims benefit of provisional application No. 60/144,858, filed Jul. 20, 1999.

FIELD OF THE INVENTION

This invention relates to an apparatus and a method that facilitates safe and convenient intermittent self-catheterization of a fluid-containment body cavity by a user. More particularly, it relates to an apparatus and a method by which a female patient is initially prepared by her doctor and thereafter is enabled, safely and without further medical help, to intermittently insert a catheter into her urinary bladder to comfortably void urine as needed.

BACKGROUND OF THE RELATED ART

There are many circumstances, e.g., after pelvic reconstructive surgery and/or anti-incontinence surgery, abdominal trauma or hernia, urinary infection, or the like, which can result in unpredictable delays in urination and may require that a female patient be provided with a catheter to enable her efficiently to void urine from her bladder either as her needs dictate or continuously.

Initially, generally during a time when the patient is recuperating in a hospital and under medical observation, it may be desirable to provide for constant drainage of urine from her bladder. Sometimes such a need continues even after recuperation, and the healed patient may for a long time have to wear a catheter that provides continuous drainage of urine into a receptacle like a small bag that is worn on the body and has to be periodically replaced. There are certain problems and discomforts associated with this. For example, ambulatory patients typically have their urine-collection bag strapped to a leg so that it is lower than the pelvis, and urine flow is gravity-driven down into the bag. This can be physically awkward, can be unsightly, and may adversely affect the user's psychological sense of well-being.

A commonly used catheter for continuous drainage of urine is some form of the indwelling Foley catheter, a distal end of which is inserted into the user's bladder through her urethra and is thereafter retained in place by inflation of a balloon-like element. This type of catheter is known to cause discomfort and irritation of the trigone, often causing bladder spasm. Often the catheter must be replaced by a doctor after removal due to continued bladder dysfunction. Various improvements have been suggested to alleviate the problems of tissue compression, irritation, infection and the like that are sometimes encountered in use of the Foley catheter, for example, as disclosed in U.S. Pat. No. 5,562,622, to Tihon, titled "Self-cleansing Bladder Drainage Device". U.S. Pat. No. 4,738,667, to Galloway, titled "Preformed Catheter Assembly" offers an alternative structure, in which the continuously draining catheter has a pre-curved distal end shape which, after its placement in functional position, tends to retain it in the bladder without a balloon or the like. A somewhat similar solution is taught in U.S. Pat. No. 3,490,456, to Kortum, titled "Intrauterine Catheter Anchor". Among the complications that, while rare, can occur in the placement and use of a suprapubic catheter are hematuria, cellulitis, bowel injury, urine extravasation, and catheter fracture.

Another alternative for continuous drainage is the use of a suprapubic catheter, but this too has its own problems and is not particularly favored by patients.

Intermittent self-catheterization, a third alternative, is often difficult for many patients to perform, as they may not readily be able to locate the urethra.

It is considered that the ideal mechanism would be one which will enable the patient to void spontaneously and conveniently, to check the efficiency of her voiding, and to be so comfortable and manageable that she can do all this entirely on her own and free of the need to repeatedly call or visit her doctor. The mechanism and the method of using it should be safe, and should not lead to any infection rates higher than those encountered with conventional catheter systems.

The present invention is intended to fulfill this long felt but hitherto unmet need.

SUMMARY OF THE INVENTION

A principal object of this invention is to provide apparatus that enables a female who suffers from a urinary control problem to obtain efficiently, safely and comfortably intermittent drainage of urine from her bladder without assistance from others.

A further object of the invention is to enable a doctor of a female patient having urinary control problems to provide her with an efficient, safe and simple apparatus that enables her to obtain intermittent voiding of her bladder by herself, without discomfort and without incurring a higher risk of infection than is associated with known catheter systems.

A related object according to another aspect of this invention is to provide a method by which a female can be enabled to intermittently, safely and comfortably void urine efficiently when her natural urinary function is adversely affected or is dysfunctional.

A further related object of the invention is to provide a method by which a female who has problems voiding urine can obtain safe, comfortable, intermittent relief by self-catheterization after an initial catheterization by her doctor.

Accordingly, in a first aspect of this invention there is provided a catheter guidewire or other thin, flexible guide element that is initially placed substantially within a female patient's body by a doctor or other qualified person and is thereafter worn internally by her. The guide element includes a flexible distal end portion having an unstrained shape formed thereat or other features that allow the guide element to remain located within a fluid-containment body cavity following placement therein, and has a proximate end portion extendable out of an opening of the fluid-containment cavity. A proximate end of the guide element, during its use, is preferably shaped to be comfortably accessible by the user for insertion into a distal end of a catheter to guide the catheter into the opening of the fluid-containment cavity for voiding of fluid therefrom via the catheter along and past the guide element. A particularly beneficial application of this embodiment is realized when the guide element is located with its distal end portion in an unstrained form entirely within the urinary bladder of a female patient. The proximate end portion of the guide element adjacent the distal end portion would then be held non-leakingly in the urinary sphincter and the urethra, but would permit the user to void volitionally to the extent possible, with the proximal end of the guide element located substantially within or close to the user's vagina where she can access it easily to guide a catheter along the guide element into her bladder when she needs to void urine more completely.

In another aspect of the invention, there is provided a catheter system that comprises an initial placement tubular catheter and a cooperating guide element that is functionally disposed by a doctor or other qualified personnel within a female patient's body via the tubular catheter to guide subsequently used catheters. The guide element has a flexible distal end portion, which in an unstrained state has a flexibly deformable shape and size selected for retention within a fluid-containment cavity of the user's body, or other features for retaining the distal end portion, and a proximal end portion functionally disposable so that a proximate end thereof is readily accessible to the user. The elongate lumen of at least the initial placement catheter is sized to facilitate easy sliding conveyance therethrough of the entire length of the guide element even while, for example, the distal end portion is in a strained state. A particularly beneficial realization of this aspect of the invention involves an initial introduction of a distal end of a first catheter, via the user's vagina and urethra, into her urinary bladder by a doctor or other qualified personnel. This is followed, for example, by the forcible introduction of the distal end portion of the guide element through the proximal end of the catheter, with elastic straining of at least the distal end portion of the guide element, until all of the proximal end portion is within the bladder and is able to recover its unstrained shape. The proximal end portion of the guide element adjacent the distal end portion would then be held in place by the user's urinary sphincter and urethra upon removal of the initial placement catheter, and the proximate end of the guide element would then be disposed substantially within or close to the user's vagina and be readily accessible to her. The user would then be able to safely and comfortably guide the distal end of another catheter by herself along and around the guide element into her bladder to be able to void urine as needed.

In a further related aspect of this invention, the proximate end of the guide element has a somewhat enlarged bulbous end sized to slide easily within the lumen of the catheter to be used by the patient, and that catheter is provided with a lateral opening and is fitted with a perforate ramp to facilitate movement of the bulbous proximate end of the guide element out of the lateral opening for convenient handling by the user.

In another aspect of this invention, there is provided a method of safely and conveniently voiding urine from a female's urinary bladder, comprising the steps of: placing by a qualified person of a preshaped elastically deformable distal end portion of a guide element, via a first catheter, through her urethra into her bladder and nonleakingly extending a proximate end portion of the guide element out of her urethra for ready access thereto by her; and guiding by the female herself of at least a second catheter along the proximate end portion of the guide element to her urethra and thus into her bladder to void urine through at least the second catheter.

In a further related aspect of this invention, there is provided a method of efficient, safe and convenient urinary self-catheterization by a female, comprising the step of having an elastically deformable distal end portion of a guide element of a predetermined shape located within her urinary bladder, with a proximal end portion of the guide element extended via her urinary sphincter and urethra so that a proximate end of the guide element is functionally disposed to be easily accessible to her to enable her by herself to guide a catheter along the guide element through her urethra into her bladder to be able to void urine as needed.

These and other related aspects and benefits of the disclosed invention and its obvious variations will be better understood from the detailed description provided below with appropriate reference to the appended drawing figures.

BRIEF DESCRIPTION OF THE DRAWINGS

FIG. 1 is a first side elevation view of a first preferred embodiment of a guide element according to this invention;

FIG. 2 is an end view of the guide element of FIG. 1;

FIG. 3 is a second side elevation view of the guide element of FIG. 1, at a 90 degree rotation relative thereto;

FIG. 12 is a perspective side view of a patient-use catheter and guide element combination (with the entire length of the guide element not shown for convenience), in accordance with a second preferred embodiment of the invention;

FIG. 13 is a partial perspective view of a bulbous proximate end of the guide element according to the second preferred embodiment per FIG. 12;

FIG. 14 is a partial perspective view of the distal end portion of the patient-use catheter according to the second preferred embodiment per FIG. 12;

FIG. 15 is a partial longitudinal axial cross-sectional view of the proximate end of the guide element just introduced into the distal end of the patient-use catheter according to the second preferred embodiment per FIG. 12;

FIG. 16 is a perspective view of a preferred form of a perforate element to be located within the patient-use catheter to guide the bulbous proximate end of the guide element sideways out of the lateral opening provided immediately forwardly of the perforate element, according to the second preferred embodiment per FIG. 12; and FIG. 17 is a view of the initial insertion of the catheter guide element using a suitable rod in accordance with an embodiment of the present invention.

DETAILED DESCRIPTION OF THE PREFERRED EMBODIMENTS

Figure 4:
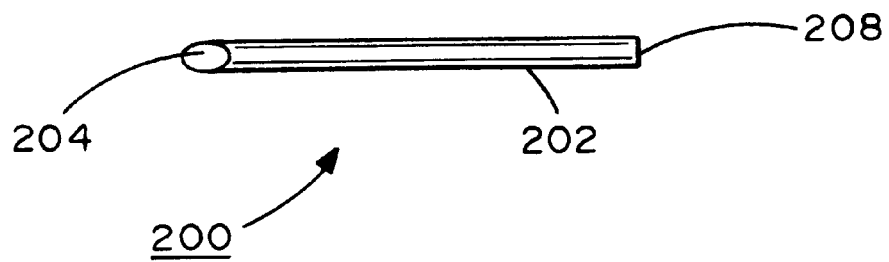
FIG. 4 is a first side elevation view of an initial placement catheter according to a first preferred embodiment thereof per this invention.

FIGS. 1, 2 and 3 illustrate the principal structural features of a guide element 100 formed according to a preferred embodiment of this invention. It is preferably a selected length of smooth-walled solid wire of uniform cross-section and is free of sharp edges, kinks or surface roughness under all conditions of intended use. It is preferably treated to ensure that the end peripheries are smoothly rounded. Distal end 102, for a preferred embodiment discussed below, is formed to have the shape of a bulb. This may be done by briefly melting the guide element material there or by fitting a small bulb as best seen in FIG. 13. The bulb preferably has a maximum diameter about two to four times the guide element itself.

Guide element 100 in this preferred embodiment, when in an unstrained state, comprises a generally conical spiral-spring shaped distal end portion 104 ending at a maximum radius "R" relative to an axis W—W, as best understood with reference to FIG. 2. The length of distal end portion 104 is "S", as best seen in FIG. 3. Guide element 100 also comprises a proximate end portion 106 which preferably ends in a curve 108 of a radius "r", as best seen in FIG. 3. The length "L" of proximal end portion 106 between distal end portion 104 and curve 108 may be essentially elongate, and is not given a particular shape as such.

A preferred cross-sectional dimension for guide element 100 is 2 French, which is less than 0.5 mm, hence for the most suitable materials the entire length of guide element 100 is in fact quite flexible in bending. However, when it is guided through the lumen of a suitably sized catheter it can easily be pushed or pulled for proper disposition for use, as is described below in detail. The lumen of any catheter through a length of which the guide element 100 is to be passed must have an internal diameter slightly larger than the maximum diameter of bulbous end 102.

Persons of ordinary skill in the uro-gynaecological arts will appreciate that customization of size may be an important factor in the success of any device that has to be worn internally by a patient. It should therefore be understood that the various dimensions relating to guide element 100 should be selected by the treating physician to best suit the patient. For most adult females, however, generally satisfactory dimensions are as follows: R=0.38 in, r=0.75 in, S=1.00 in and L=6.00 in.

Figure 5:
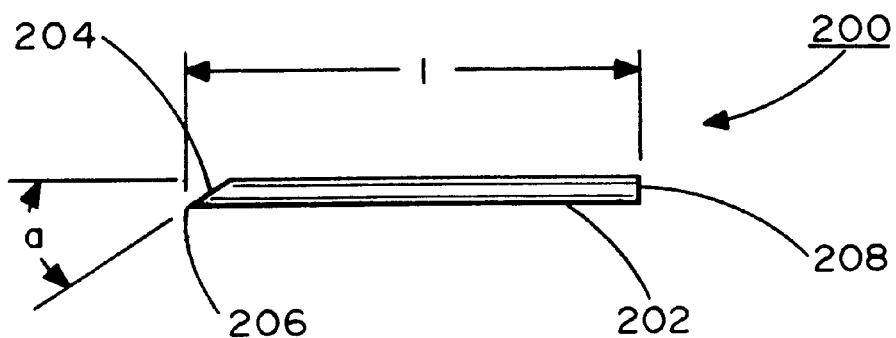
FIG. 5 is a second side elevation view of the initial placement catheter of FIG. 4, at a 90 degree rotation relative thereto.
Figure 6:
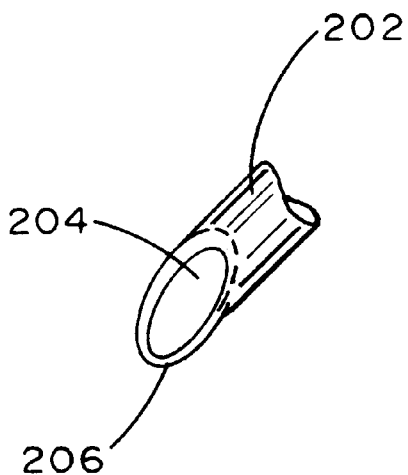
FIG. 6 is an enlarged perspective end view of the distal tip of the initial placement catheter of FIG. 4.
Figure 7:
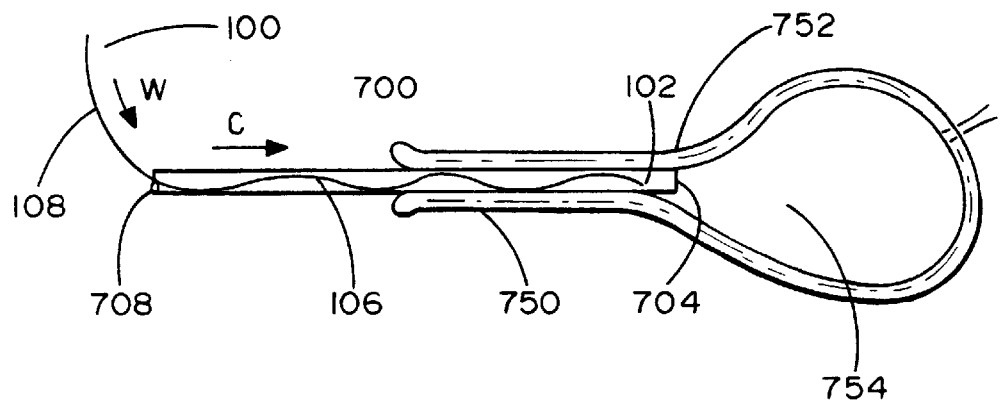
FIG. 7 is a schematic longitudinal cross-sectional view of an initial placement catheter and guide element combination according to the first preferred embodiment, to illustrate the relative disposition thereof as it is being initially introduced into the user female's bladder prior to location of the guide element for its functional purpose.
Figure 8:
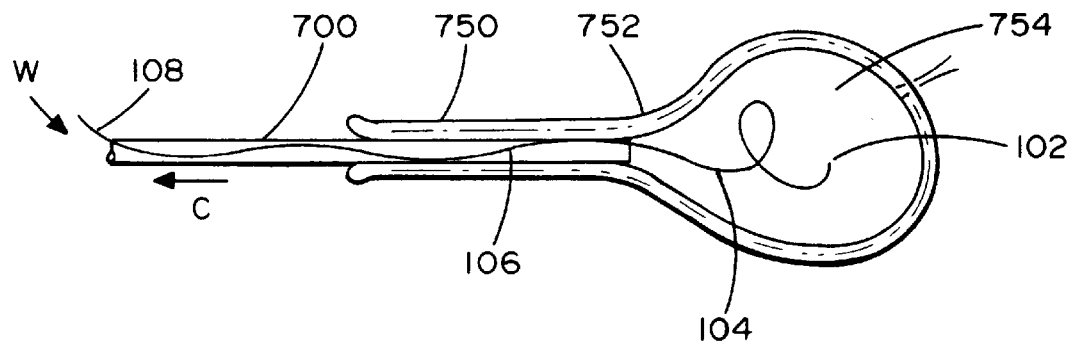
FIG. 8 is a similar view to illustrate a state in which the guide element has been disposed inside the bladder and the catheter of FIG. 7 is being withdrawn.

FIGS. 4, 5 and 6 illustrate important features, in a first preferred embodiment, of both an initial placement catheter used by the doctor to place the guide element 100 inside the patient as well as other catheters to be used by her in subsequent use of the guide element 100 to void urine without help from others such as her doctor, trained nurses or paramedicals. Other known simple tubular catheters, e.g., those with differently shaped distal ends, may also be used with the guide element 100 as described below. In addition, other known features for retaining the guide element 100, other than the curved form shown in the figures of this embodiment, may be used or understood to those knowledgeable in the art without departing from the scope of the invention.

Catheter 200, according to the first embodiment, is essentially a simple elongate tube, of length "1" preferably about 4.00 in, and is typically made of a polypropylene material. It may, in its simplest form, have a circular lumen of a diameter from four to five times the diameter of guide element 100. The outside surface 202 of catheter 200 should be smooth and free of any kinks or roughness. In the first preferred embodiment per FIGS. 4, 5 and 6, the distal end 204 of catheter 200 is cut at an angle "a" which preferably is in the range 20 to 30 degrees relative to the longitudinal axis (not shown). The peripheral edge 206 of the distal end 204 should be made smoothly rounded and free of any sharpness in order to avoid damage to the patient's tissues during use. Proximal end 208 also should be provided a sharpness-free periphery, but does not have to be cut at any particular angle as it should not in normal use be likely to press on the patient's tissues.

The first preferred embodiment should be comfortably handled by a patient who has some manual dexterity and is otherwise physically fit. However, there are patients who may be relatively enfeebled, overweight, stiff, or otherwise limited in their ability. The second preferred embodiment is intended to assist such users, and generally all users, in more conveniently using the present invention.

As best seen in FIGS. 12–16, in this form of the catheter system, the patient use catheter 1200 has a slant-cut distal end 1204 with rounded edges as before. However, at its proximate end 1206, there is provided an enlarged diameter outside grip element 1208, which may preferably comprises a soft, non-slip material and/or outer surface texture. The length of grip element 1208 may be about 0.5 in. and its outer diameter preferably about two to three times the outer diameter of the catheter body 1202.

Patient-use catheter 1200 is formed to have a lateral opening 1210 about 0.4–0.5 in. inboard of distal end 1204, oriented preferably as shown, for reasons explained below. Guide element 1300, as indicated in FIGS. 12 and 15, may be introduced at its proximate end into distal end 1204 of the patient-use catheter 1200 for their intended confirmed use, i.e., to enable the patient to slidingly guide the catheter 1200 into her urethra for access to her bladder to void therefrom.

As best seen in FIG. 13, the guide element 1300 is provided at its proximate end with an enlarged-diameter, smoothly-rounded, bulbous form 1302. This, as indicated, may be done by forming the guide element to the required shape, e.g., by known forming techniques or even by heating the guide element material locally to melting point and cooling so that the material coalesces to the desired enlarged smooth shape. What is important is that the maximum diameter of bulbous form 1302 be larger than that of the guide element 1300, preferably two to four times the size of the latter, yet somewhat smaller than the internal diameter of catheter 1200, so that it may slide smoothly within the lumen thereof.

FIG. 14, in enlarged perspective view, is intended to clarify that opening 1210 preferably has a somewhat teardrop shape, with its smallest diagonal being larger than the maximum diameter of bulbous form 1302 at the proximate end of the guide element 1300. The rear edge 1212 of opening 1210 is formed to have a rearwardly sloping surface to assist in the ramping of bulbous form 1302. Both features serve to allow bulbous form 1302 easy passage through opening 1210 in either direction, i.e., sideways out of opening 1210 when the patient pushes the guide element 1300 into the catheter 1200 and also when the patient removes the catheter 1200 after voiding urine and leaves the guide element 1300 in place for subsequent use to again guide the catheter 1200 into her urethra. This relative motion is indicated by arrows "WW."

To ensure that bulbous form 1302 will readily emerge through opening 1210, there is fitted into the lumen of catheter 1202 a perforate ramping element 1600, one preferred form of which is best seen in FIG. 16. Ramping element 1600 has an outside surface 1602 of a diameter that ensures at least a very tight friction fit inside the lumen of patient-use catheter 1202 under opening 1210, as best seen in FIG. 15. Ramping element 1600, in possibly other forms as dictated by considerations of cost, ease of manufacture, and the like, may be adhered in place or have its essentials made integral with the catheter structure.

The two most important services rendered by ramping element 1600 are to provide a least one opening 1603 to permit urine flow out of the catheter 1200 and to provide a smooth ramping surface 1604 along one or more edges 1606, 1606. Two such edges 1606, each with a corresponding ramping surface 1604 are shown, but persons of ordinary skill in the mechanical arts will readily consider a single edge or even single perforated ramp surface to accomplish the desired objective.

Short arrows labeled "W" indicate the direction in which ramping element 1600 should direct the proximate end of guide element 1300, and undulating arrows labeled "U" indicate the direction of urine flow, in FIGS. 15 and 16. The method of use of the second preferred embodiment will now be described.

The patient should void as much urine as she can past the implanted guide element 1300 positioned by the doctor. If she feels that voiding is incomplete, she must grasp the proximate end of guide element 1300 and insert the bulbous form 1302 thereof into distal opening 1204 of catheter 1200 until physical interaction between bulbous form 1302 and ramping surfaces 1604, 1604 diverts bulbous form 1302 sideways and out of opening 1210 along the path of arrows "W" in FIG. 15. The patient using this embodiment does not have to thread a guide element 1300 along the entire length of a catheter as was the case with the first preferred embodiment. Also, she should have an easier time grasping the bulbous form 1302 and pushing catheter 1200, slidingly guided along guide element 1300, passing via the lumen length between distal end opening 1204 and lateral opening 1210, into her urethra. She can then complete voiding by the passage of urine from her bladder via openings 1204 and 1210 (as indicated by undulating arrows "U" in FIG. 15) and out via the proximate end of catheter 1200.

Note that the methods of use of both preferred embodiments are very similar. The second preferred embodiment may be easier for some patients to use. With the second embodiment, eventual removal of the guide element 1300 from the patient's bladder will be along and via the distal end opening 1204 of catheter 1200 after her last urine voiding.

Guide element 1300, with its bulbous form 1302, may be initially placed by the surgeon after he or she has inserted the distal end of initial placement catheter 200, very easily by pushing on the bulbous form 1302 forwardly inside the lumen of catheter 200 by pressing on the same by a simple rod. As indicated in FIG. 17, a suitably sized rod 1700 can be used with an initial-placement catheter 200, by pushing in the direction of arrow "R" on a guide element 1300 suitably lubricated and initially packed inside an initial-placement catheter 200 preferably 8 in. or so long. Guide element 1300 may typically be about 6 in. long for most adult patients.

It will be readily seen that the different features of the described elements may be adapted and/or sized as best for particular patients. Known catheters made of polypropylene, for example, can be fitted with end grips, provided lateral openings, and also fitted with ramping elements using known technology. Other aspects of use of this invention, e.g., initial cleansing, sterile packing, safe lubrication during catheter insertions, etc., all also may follow well-established practices. A typical patient-use kit may include a set of patient-use catheters, a quantity of lubricant, cleansing detergent, and instructions that include simple figures.

The method of using the above-described invention according to the first preferred embodiment will now be described with particular reference to FIGS. 7–11. Short bold arrows are provided immediately adjacent to the guide element and the catheter in these figures to indicate their respective directions of movement relative to the patient's urethra in various steps of the overall procedure.

As an initial matter, the doctor and female patient must agree that intermittent self-catheterization is appropriate for her in the context discussed earlier. After the procedures that she must follow are adequately explained to her, the doctor will insert the distal end portion of a guide element 100 through the proximal end 708 of an initial placement catheter 700, which may in fact have a distal end like end 204 of catheter 200 discussed previously. This is entirely up to the doctor who, it must be remembered, should have far greater experience than the patient and should be in a better position to see whether the catheter 1700 is moving in correctly into the urethra. The doctor checks visually through the partially transparent wall of the catheter 700 and at its distal end 704 to ensure that guide element 100 is sliding freely within catheter 700, that it is not kinked, and that distal end 102 is not outside distal end 704 of the catheter 700. The doctor then carefully introduces distal end 704 via the patient's urethra 750 and urinary sphincter 752 into her bladder cavity 754. If there is urine in cavity 754 it may leak out at this time depending on the physical position of the patient. This would probably be desirable and educational for the patient who would see for the first time how the catheter 700 permits urine to flow out.

Figure 11:
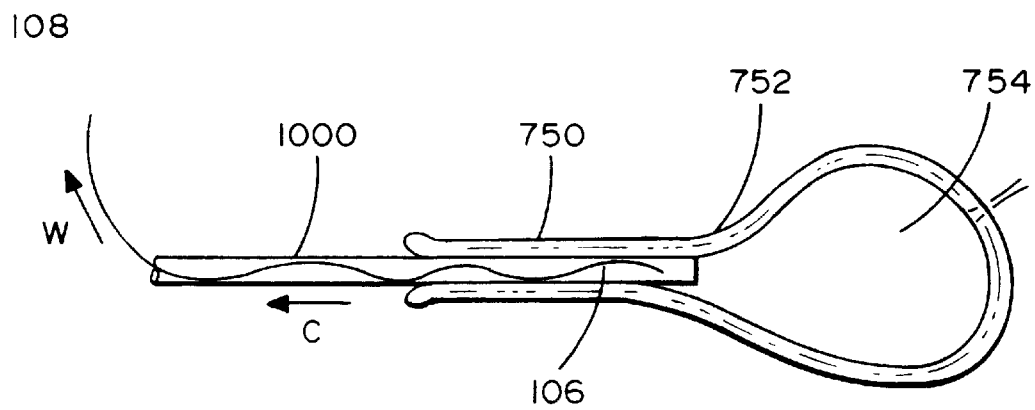
FIG. 11 is a view similar to that of FIG. 7 but to illustrate a state following that of FIG. 13 as the wire has been drawn entirely within the distal end portion of the catheter and both are safely withdrawn together from the bladder.

The doctor then advances guide element 100 further along and inside catheter 700 until the distal end portion 104 is entirely within cavity 754, as best seen in FIG. 11. Since distal end portion 104 of the guide element 100 is no longer constrained by catheter 700, it should regain its "unstrained" form (per FIGS. 1–3) while it is at the patient's internal body temperature, which should be about normal human body temperature, even if she has a slight fever, or the guide element 100 will otherwise be retained within the cavity 754 by virtue of features of the guide element 100.

Figure 9:
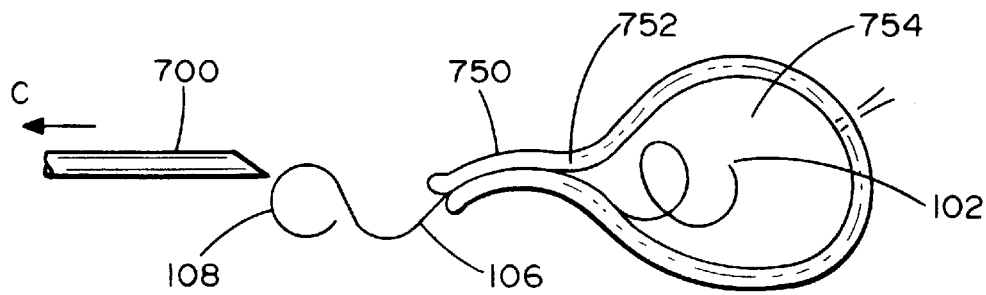
FIG. 9 is a schematic longitudinal cross-sectional view through the user's bladder, wherein the guide element is functionally disposed, as she is about to introduce the proximal end of the guide element according to the first preferred embodiment into the distal end of a patient-use catheter to guide the latter into her bladder to void urine therethrough.

The doctor then gently withdraws catheter 700 from the patient's urethra while leaving guide element 100 within her body, as best understood with reference to FIG. 9. Removal of catheter 700 results in the patient's urinary sphincter 752 and urethra 750 closing onto guide element 100 aft of distal end portion 104 thereof to hold it in a leak-free manner. The predetermined unstrained, generally conical-spring shape of distal end portion 104 or other features ensure that even if the patient moves around vigorously the guide element 100 will not fall out from where the doctor placed it for future use by her. Because distal end 104, for example, spirals to an end at its largest radius (see FIGS. 2 and 3), guide element 100 cannot advance too far into cavity 754 either. Guide element 100 is now in place for the patient's use at her discretion. Its proximal end portion 108 should preferably be in or very close to the patient's vagina and thus readily accessible to her to slide into the distal end of a catheter handled solely by her whenever she wishes to utilize the invention to urinate.

Figure 10:
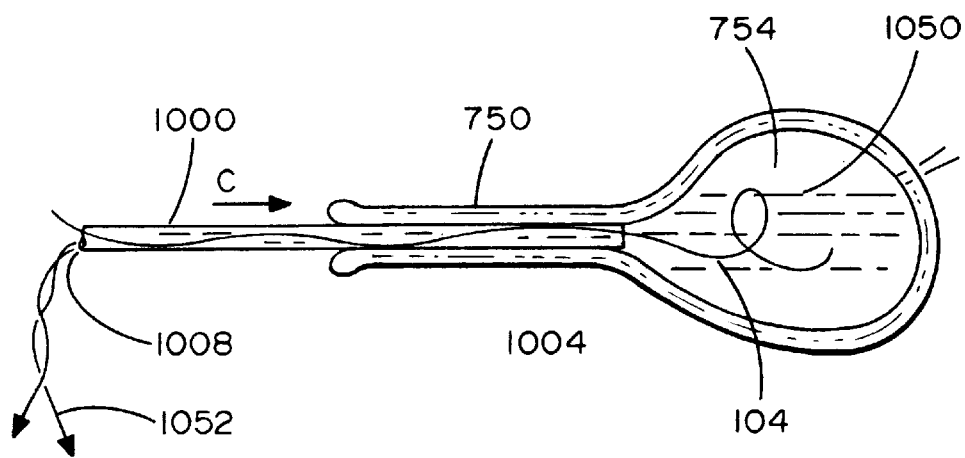
FIG. 10 is a view similar to that of FIG. 8 but to illustrate how a guide element that is to be removed from the user's bladder is carefully withdrawn via the distal end of a catheter.

As best understood with reference to FIG. 10, to use the apparatus per the first preferred embodiment for its intended purpose the patient pushes a catheter 1000, which may be like catheter 200 as discussed previously, along and around the proximal end portion 108, 106 of guide element 100 until the distal end 1004 of the catheter enters her urinary cavity 754. The cross-section of the lumen of the catheter 1000 is larger than the cross-section of guide element 100, hence there is room for urine 1050 from cavity 754 to emerge as urine flow 1052 out of the proximal end 1008 of catheter 1000. When she has completed urination, the patient needs simply to withdraw catheter 1000 from her urethra, which will then revert to the state illustrated in FIG. 9 where it non-leakingly closes onto and holds the guide element 100 in place for future use.

Once the guide element is in place, the patient should attempt to void urine as and when she feels a need to do so. Some urine should flow past guide element 100 out of her urethra. If she feels that she has not voided satisfactorily, she should utilize catheter 1000 as described in the immediately preceding paragraph. The doctor should advise her on such details, and she should perhaps keep a record of the extent to which use of the catheter helps her. Eventually, the need for the catheter may disappear.

When the patient has fully recovered her urinary bladder control, and no longer needs to use this invention, she can insert the catheter 1000 one last time as before and this time withdraw guide element 100 and catheter 1000 together out of her urethra. This is best understood with reference to FIG. 11.

The key to the success of the invention is that guide element 100 can be significantly deformed, and thus mechanically strained during use by being forced to pass into the rather small lumen of the enveloping initial placement catheter, without losing its ability to deploy its distal end portion 104 in the shape selected to enable it to be safely retained within the patient's bladder. This requires that the material of which guide element 100 is made be carefully chosen not just for its compatibility in the human body in prolonged presence of urine, but also for its ability to tolerate severe physical deformations without losing its predetermined selected shape. A number of materials commonly known as "super elastic materials" are considered to be particularly suited for this purpose. Their most interesting feature is that they can be drawn into wires or other similarly shaped guide elements of acceptable dimensions for the purposes of this invention and exhibit the desired ability to undergo severe mechanical deformation and still recover their predetermined shape upon being relieved of prolonged strain before placement into the patient for her use.

U.S. Pat. No. 5,238,004, to Shahatjian et al., titled "High Elongation Linear Elastic Guidewire", discusses a number of such materials. At column 1, lines 48–54, for example, it notes that: "Because of the high elongation of the super-elastic materials, a guidewire which has been previously curved deformed can be straightened when being introduced to the body through a needle and then will restore itself to the original shape when inserted in a blood vessel". Numerous alloys, including one comprising nickel and titanium and commonly called "Nitinol", are discussed in detail in this patent, and the relevant portions thereof are incorporated herein by reference. "Nitinol" is also identified in U.S. Pat. No. 5,111,829, to de Toledo, titled "Steerable Highly Elongated Wire", as "super elastic, flexible, and kink-resistant", all properties that the guide element 100 of this invention must have. The structure of the guidewire taught in Shahatjian et al. is formed from precursors of superelastic alloys, i.e., materials that have the same chemical constituents as superelastic materials but have not been processed to impart the superelastic property, and is otherwise different from the guide element structure taught herein.

"Nitinol" is also known to be treatable so that it will have a first shape at a first temperature but will revert to an earlier different shape when subjected to a change in its temperature. With such a material, guide element 100 could be formed to have the preferred shape per FIGS. 1–3 at about normal human body temperature but to be essentially straight at a lower temperature. It could then be kept cool and straight until needed and then be very easily slipped in via the placement catheter by the doctor so that distal end portion 104 quickly recovers its desired shape upon being warmed in the patient's urinary bladder. This would avoid having to force a deformation on the distal end portion in getting it to its functional location. Any deformation of the rest of the guide element 100 is less critical to its safe retention in its functional position.

What is worthy of note is that suitable materials for guide element 100 are known and are generally available.

Although it is not considered essential, it may be desirable to provide guide element 100 with a low-friction coating of a polymer material such as polytetrafluoroethylene (often called "Teflon™") to ease its passage into and out of the catheters during prolonged use.

Persons of ordinary skill in the relevant art, upon developing an understanding of the invention disclosed herein, will undoubtedly consider obvious variations thereof. All such variations are intended to be comprehended within this invention, which is limited solely by the claims appended below.

What is claimed is:

1. A catheter guide element, comprising:
   a flexible distal end portion having a predetermined shape when in an unstrained state, said shape being selected to ensure that the distal end portion tends to remain safely located within a fluid-containment body cavity of a user upon placement therein; and
   a proximate end portion extendable from said body cavity, sized so that the proximate end thereof during use is readily accessible by a user to guide a user-held catheter along said proximate end portion into a body cavity.

2. The guide element according to claim 1, wherein:
   the proximate end portion is long enough to extend through and out of a proximate end of the catheter.

3. The guide element according to claim 1, wherein:
   the distal end of the guide element is free of sharpness, and the proximate end of the guide element is provided with a smoothly rounded bulbous form.

4. The guide element according to claim 3, wherein:
   the bulbous form at the proximate end of the guide element has a maximum diameter between three and four times the diameter of the guide element.

5. The guide element according to claim 3, wherein:
   the guide element is approximately 5 inches long.

6. The guide element according to claim 1, further comprising:
   a smooth and kink-free external surface.

7. The guide element according to claim 1, further comprising:
   a coating having a smooth low-friction external surface.

8. The guide element according to claim 7, wherein:
   the coating comprises a polytetrafluoroethylene.

9. The guide element according to claim 1, wherein:
   the guide element comprises a super-elastic material.

10. The guide element according to claim 1, wherein:
    the guide element comprises a material that can in an unstrained state have different selected shapes at different temperatures.

11. The guide element of claim 10, wherein the material comprises wire.

12. The guide element according to claim 1, wherein:
the distal end portion comprises a generally conical helical shape when in an unstrained state at about or a little above normal human body temperature.

13. The guide element according to claim 1, wherein:
the guide element has a diameter of about 2 French.

14. The catheter system of claim 1, wherein:
the guide element comprises a guidewire.

15. A guide element catheter system, comprising:
a tubular first catheter; and
a guide element having a flexibly deformable distal end portion which in an unstrained state has a predetermined shape and size selected to be safely retained within a fluid-containment cavity of a user's body during use, the guide element also having a proximate end portion with an end shaped and sized to enable easy access by the user to the proximate end thereof from outside the cavity, the entire guide element being sized and shaped to be readily slidable within the first catheter even when the distal end portion is in a strained state.

16. The catheter system according to claim 15, wherein:
the first catheter has a distal end that is shaped and sized for easy insertion into the fluid containment cavity, and has an internal first lumen that is shaped and sized to permit easy removal of the first catheter relative to the proximate end portion of the guide element without removing a fluid containment distal end portion from the cavity after placement therein.

17. The catheter system according to claim 15, wherein:
the guide element is initially located entirely inside a lumen of the first catheter.

18. The catheter system according to claim 17, wherein:
the proximate end of the guide element is provided with a smoothly rounded bulbous form having a maximum diameter smaller than a diameter of the lumen of the catheter.

19. The catheter system according to claim 18, further comprising:
an elongate element insertable into the lumen of the first catheter so as to press against said bulbous form of the guide element contained therein and to thereby move at least the distal end portion of the guide element out of the distal end of the lumen and into the cavity.

20. The catheter system according to claim 19, wherein:
the elongate element is formed to enable a user to determine when the elongate element has been inserted into the lumen of the far enough to have moved at least the distal end portion of the guide element into the cavity.

21. The catheter system according to claim 17, wherein:
the first catheter and the guide element are each at least about 8 inches long.

22. The catheter system according to claim 15, further comprising:
at least a tubular second catheter, having an internal second lumen shaped and sized to permit easy passage thereof over and around the proximate end portion of said guide element following placement thereof in a patient's body to be guided thereby into the cavity under the user's control until fluid is enabled to flow out of the cavity via the second lumen.

23. The catheter system according to claim 22, wherein:
the first catheter has an angled distal end with a smoothly rounded outer edge.

24. The catheter system according to claim 22, wherein:
a lateral aperture with a rearwardly ramping rear edge portion is provided through a wall portion of the second catheter near a distal end thereof, and further comprising a rearwardly ramping surface disposed under said lateral aperture to guide the proximate end of the guide element via the lateral aperture.

25. The catheter system according to claim 23, wherein:
a lateral aperture with a rearwardly ramping rear edge portion is provided through a wall portion of the second catheter near a distal end thereof, and further comprising a rearwardly ramping surface disposed under said lateral aperture to guide the proximate end of the guide element via the lateral aperture.

26. A self-catheterization system, comprising:
an elongate guide element having a deformable elastic distal end portion which in an unstrained state has a predetermined shape and size selected to be safely retained within a fluid-containment cavity of a user's body during use following initial placement therein, the guide element having a proximate end position with a bulbous end sized and shaped to facilitate user access and handling thereof from outside the cavity;
an initial placement catheter having a length and an internal lumen shaped and sized to initially contain the entire guide element within;
an initial placement element slidable within the lumen of the initial placement catheter to move the guide element therein for placement of the distal end portion within the cavity for use thereafter by the user; and
a patient-use catheter having a distal end and a proximate end with an internal lumen extending therebetween, formed to have a lateral opening near the distal end and provided with an internal ramping surface disposed to direct the bulbous end of the guide element in movement thereof via the lateral opening while permitting fluid flow from the distal end and the lateral opening to pass via the lumen to the proximate end of the patient-use catheter.

* * * * *